US012691164B2

(12) United States Patent
Lin et al.

(10) Patent No.: US 12,691,164 B2
(45) Date of Patent: Jul. 28, 2026

(54) POLYETHYLENE GLYCOL LIPID AND USE THEREOF

(71) Applicant: JENKEM TECHNOLOGY CO., LTD. (TIANJIN), Tianjin (CN)

(72) Inventors: Meina Lin, Tianjin (CN); Shuzhen Hu, Tianjin (CN); Changyou Zhu, Tianjin (CN); Qingbin Wang, Tianjin (CN); Jie Wang, Tianjin (CN); Hongli Jia, Tianjin (CN); Xiaomeng Chen, Tianjin (CN); Xuan Zhao, Tianjin (CN)

(73) Assignee: JENKEM TECHNOLOGY CO., LTD. (TIANJIN), Tianjin (CN)

( * ) Notice: Subject to any disclaimer, the term of this patent is extended or adjusted under 35 U.S.C. 154(b) by 285 days.

(21) Appl. No.: 18/573,699

(22) PCT Filed: Feb. 21, 2022

(86) PCT No.: PCT/CN2022/076994

§ 371 (c)(1),
(2) Date: Dec. 22, 2023

(87) PCT Pub. No.: WO2023/273364

PCT Pub. Date: Jan. 5, 2023

(65) Prior Publication Data

US 2024/0350640 A1 Oct. 24, 2024

(30) Foreign Application Priority Data

Jun. 30, 2021 (CN) ........................ 202110741956.7

(51) Int. Cl.
*A61K 47/34* (2017.01)
*A61K 31/7088* (2006.01)
(Continued)

(52) U.S. Cl.
CPC .......... *A61K 39/00* (2013.01); *A61K 31/7088* (2013.01); *A61K 39/12* (2013.01);
(Continued)

(58) Field of Classification Search
None
See application file for complete search history.

(56) References Cited

U.S. PATENT DOCUMENTS

2014/0326600 A1 11/2014 Li et al.
2017/0157268 A1* 6/2017 Ansell .................. C07C 227/16
(Continued)

FOREIGN PATENT DOCUMENTS

CN 102068701 A 5/2011
CN 102665685 A 9/2012
(Continued)

OTHER PUBLICATIONS

Park, E.J., et al., Emerging PEGylated non-biologic drugs, Expert. Opin. Emerg. Drugs, 24 (Apr. 19, 2019) pp. 107-119. (Year: 2019).*
(Continued)

*Primary Examiner* — Dominic Lazaro
(74) *Attorney, Agent, or Firm* — NIXON & VANDERHYE, PC

(57) ABSTRACT

A new typepolyethylene glycol lipid and the use thereof. The lipid is free of in-vivo cleavable bonds, and can deliver a bioactive substance to a target cell or organ more stably. In addition, the new typepolyethylene glycol lipid can be positively charged in a specific pH environment, and can more easily form stable particles with the bioactive substance, so that the bioactive substance plays a role in the target cell or organ.

14 Claims, 2 Drawing Sheets

Specification includes a Sequence Listing.

(51) Int. Cl.
*A61K 39/00* (2006.01)
*A61K 39/12* (2006.01)
*C08G 65/333* (2006.01)

(52) U.S. Cl.
CPC ........ *A61K 47/34* (2013.01); *C08G 65/33306* (2013.01); *A61K 2039/53* (2013.01)

(56) References Cited

U.S. PATENT DOCUMENTS

| | | | | |
|---|---|---|---|---|
| 2020/0163878 | A1* | 5/2020 | Baumhof | A61K 9/19 |
| 2020/0197510 | A1 | 6/2020 | Ciaramella et al. | |
| 2021/0154148 | A1 | 5/2021 | Benenato et al. | |

FOREIGN PATENT DOCUMENTS

| | | | |
|---|---|---|---|
| CN | 106187789 | A | 12/2016 |
| CN | 106795096 | A | 5/2017 |
| CN | 113402405 | A | 9/2021 |
| WO | 2005026372 | A1 | 3/2005 |
| WO | 2012099755 | A1 | 7/2012 |
| WO | 2019089828 | A1 | 5/2019 |
| WO | 2020061295 | A1 | 3/2020 |
| WO | 2021030701 | A1 | 2/2021 |
| WO | 2021055835 | A1 | 3/2021 |

OTHER PUBLICATIONS

International Search Report for PCT/CN2022/076994 dated May 12, 2022, 8 pages.

Written Opinion of the ISA for PCT/CN2022/076994 dated May 12, 2022, 6 pages.

* cited by examiner

Blank control

ALC-0315&DMG

Naked mRNA control

ALC-0315&DTDA

Positive control

ALC-0315&DTDAM

SEQUENCE LISTING

<160> NUMBER OF SEQ ID NOS: 1

<210> SEQ ID NO 1
<211> LENGTH: 21
<212> TYPE: RNA
<213> ORGANISM: Artificial Sequence
<220> FEATURE:
<223> OTHER INFORMATION: target sequence

<400> SEQUENCE: 1
ggcuacgucc aggagcgcac c 21

POLYETHYLENE GLYCOL LIPID AND USE THEREOF

CROSS-REFERENCE TO RELATED APPLICATION

This application is the U.S. national phase of International Application No. PCT/CN2022/076994 filed Feb. 21, 2022 which designated the U.S. and claims priority to CN 202110741956.7 filed Jun. 30, 2021, the entire contents of each of which are hereby incorporated by reference.

REFERENCE TO SEQUENCE LISTING SUBMITTED ELECTRONICALLY

The content of the electronically submitted sequence listing (Name: 8575-48_Sequence_Listing.txt, Size: 1 KB, and Date of Creation: Dec. 22, 2023) is herein incorporated by reference in its entirety.

TECHNICAL FIELD

The present invention belongs to the field of biomedicines, and particularly relates to a polyethylene glycol lipid compound and use thereof in the delivery of a bioactive substance.

BACKGROUND

With the progress of biotechnology in recent years, gene therapy drugs have achieved rapid development, bringing huge development prospects to the field of biological drugs. American Alnylam company developed a series of gene drugs by adopting RNAi technology and successfully marketed four RNAi drugs: Onpattro (patisiran), Givlaari (givosiran), Oxlumo (lumasiran) and Leavio (inclisiran), wherein Leavio (inclisiran) is a biological drug for treating hyperlipidemia, and the successful marketing of the drug widens the field of gene therapy from the traditional field of treating rare genetic diseases to the field of treating common diseases, which brings new opportunities for RNAi drugs.

Nucleic acid drugs, due to their intrinsic properties such as electronegativity, susceptibility to degradation by nucleases, etc., cannot efficiently penetrate cell membranes into cells and are rapidly degraded in vivo, so a good delivery system is required to stably deliver nucleic acids to a target site and take effect. A common difficulty in the development of mRNA and siRNA is how to deliver them efficiently into cells at the target site. During the delivery process, it is also necessary to consider how to avoid rapid clearance, avoid degradation by nucleases, and improve escape after endocytosis.

At present, the delivery systems for nucleic acids mostly use different types of liposomes, e.g., lipid nanoparticles (LNPs), GalNac, lipopolyplexes (LPPs), etc., for delivery. LNPs are generally prepared from four types of lipids in a certain proportion, the four types of lipids typically including a cationic lipid, a neutral lipid, a steroid lipid, and a polymer conjugated lipid, wherein the polymer conjugated lipid refers to a polyethylene glycol lipid. The preparation process of LNPs is relatively complex, including simply the preparation of lipid nanoparticles, RNA encapsulation cultivation, dialysis, freeze-drying, and other processes.

Polyethylene glycol (PEG) lipids have been widely reported. For example, patent documents CN106795096A, WO2005026372A1, WO2020061295A1, CN102665685A, US20210154148A1, WO2012099755A1, etc. have all disclosed a polyethylene glycol lipid compound and use of a lipid in the preparation of a lipid nanoparticle or a lipid mixture for delivering a bioactive substance into a body.

Patent document US20200197510A1 discloses a respiratory virus ribonucleic acid vaccine and a combination vaccine, and a method for using a vaccine and a composition comprising the vaccine.

Patent document CN102068701A discloses use of a cleavable polyethylene glycol lipid derivative in the preparation of a PEGylated formulation for reducing or avoiding accelerated blood clearance.

However, existing polyethylene glycol lipids, e.g., PEG-DMG and ALC-0159 (M-DTDAM), which have been disclosed in the documents as described above, all contain cleavable connecting bonds in vivo and are unstable in vivo, thereby affecting the delivery efficiency for bioactive substances.

SUMMARY

In order to overcome the defects in the prior art, the present invention provides a new type polyethylene glycol lipid, wherein the lipid is free of in-vivo cleavable bonds (e.g., an ester bond, an amide bond, etc.), and can deliver a bioactive substance to a target cell or an organ more stably. In addition, the new typepolyethylene glycol lipid can be positively charged in a specific pH environment, and can more easily form stable particles with the bioactive substance, so that the bioactive substance plays a role in the target cell or organ.

In a first aspect, the present invention provides a polyethylene glycol lipid having a structure of formula I below:

Formula I

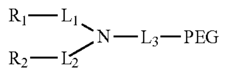

wherein $R_1$ and $R_2$ are identical or different long chain hydrocarbyl, and preferably, the long chain hydrocarbyl contains 8-25 carbon atoms;

PEG is a polyethylene glycol chain;

$L_1$, $L_2$ and $L_3$ are absent or are in-vivo non-cleavable linkers.

Furthermore, the long chain hydrocarbyl of the present invention contains 11-17 carbon atoms. For example, the long chain hydrocarbyl contains 11, 12, 13, 14, 15, 16 or 17 carbon atoms. In one embodiment of the present invention, the long chain hydrocarbyl contains 14 carbon atoms.

Furthermore, the polyethylene glycol chain of the present invention comprises a repeating unit of $-(OCH_2CH_2)_n-$, wherein the n is selected from integers of 20-300, more preferably, the n is selected from integers of 20-228, and particularly preferably, the n is selected from integers of 30-60; for example, n is selected from 30, 35, 40, 45, 50, 55 and 60.

Furthermore, the polyethylene glycol chain of the present invention is $-(OCH_2CH_2)_n-X$, wherein X is a terminal group of the polyethylene glycol chain, and is selected from methyl, methoxy, hydroxyl, amino, thiol, maleimide, etc. Preferably, X is methoxyl, and the polyethylene glycol chain is $-(OCH_2CH_2)_n-OCH_3$.

Furthermore, the in-vivo non-cleavable linker of the present invention is a relatively stable linker, and is free of in-vivo cleavable bonds, and thus is not easily degraded in an in-vivo environment. For example, the in-vivo non-cleavable linker may be a thioether linker or an alkyl linker, the alkyl linker is, for example, C1-C10 alkylene, preferably C2-C8 alkylene, and more preferably C2-C5 alkylene, the alkylene may be a linear or branched alkylene, and more preferably, the alkylene is linear alkylene, e.g., $—CH_2—$, $—CH_2CH_2—$, or $—CH_2CH_2CH_2—$.

In another aspect, the present invention provides a polyethylene glycol lipid having a structure of formula II below:

Formula II

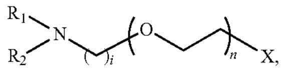

wherein $R_1$, $R_2$, X and n are as defined above, i is selected from integers of 2-7, for example, i is selected from 2, 3, 4, 5, 6 and 7, and preferably, i is selected from 2 and 3.

Furthermore, the polyethylene glycol lipid of the present invention has the following structure:

In one specific embodiment of the present invention, the polyethylene glycol lipid has the following structure:

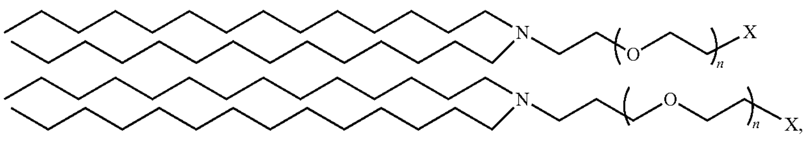

wherein X and n are as defined above, and preferably, X is $—OCH_3$.

The molecular weight of the polyethylene glycol chain of the present invention may be 1000 to 20000, preferably 1000 to 10000, for example, 1000, 1500, 2000, 2500, 3000, 3500, 4000, 4500, 5000, 5500, 6000, 6500, 7000, 7500, 8000, 8500, 9000, 9500, 10000, etc.

In a low PH solution, the polyethylene glycol lipid of the present invention can be ionized and positively charged, and can be more easily combined with phosphate groups with negative charges in RNA or mRNA.

In still another aspect, the present invention provides a method for preparing a polyethylene glycol lipid. The method comprises: reducing carbonyl in a compound of formula IV below to obtain a compound of formula II of the present invention, Formula IV

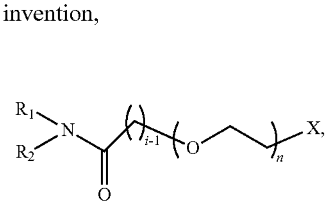

wherein $R_1$, $R_2$, X, i and n are as defined above.

Furthermore, the reducing agent for the reduction reaction is $LiAiH_4$.

Furthermore, the reduction reaction comprises: under nitrogen atmosphere, adding $LiAlH_4$ into a reaction device containing a first solvent, dissolving the compound of formula IV into a second solvent, and dropwise adding the resulting mixture into the reaction device for reaction to obtain the compound of formula II.

Furthermore, the first solvent is preferably tetrahydrofuran.

Furthermore, the second solvent is preferably tetrahydrofuran.

In one specific embodiment of the present invention, the reduction reaction comprises: under nitrogen atmosphere, slowly adding $LiAlH_4$ into a reaction device containing tetrahydrofuran, dissolving the compound of formula IV into tetrahydrofuran, slowly and dropwise adding the resulting mixture into the reaction device, dropwise adding water into the reaction system after 3 hours, filtering, concentrating the filtrate, adding isopropanol and ethyl acetate, heating for dissolving, and cooling for crystallization.

Furthermore, the compound of formula IV is obtained from a condensation reaction between a compound of formula III and

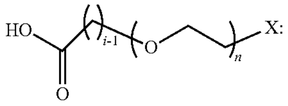

Formula (III)

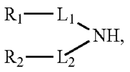

wherein $R_1$, $R_2$, X, i and n are as defined above.

Furthermore, the condensation reagent for the condensation reaction is preferably N,N,N',N'-tetramethyl-O-(7-azabenzotriazol-1-yl)uronium hexafluorophosphate (HATU).

Furthermore, the condensation reaction comprises: adding the compound of formula III and $X—(OCH_2CH_2)_n—COOH$ into a reaction device containing a third solvent, and adding N,N-diisopropylethylamine (DIEA) and HATU for reaction to obtain the compound of formula IV.

Furthermore, the third solvent is preferably dichloromethane.

Furthermore, the condensation reaction time is 3-8 hours. Preferably, the condensation reaction time is 5 hours.

Furthermore, the condensation reaction comprises: adding the compound of formula III and $X—(OCH_2CH_2)_n—COOH$ into a reaction device containing dichloromethane, stirring for dissolving, adding DIEA and HATU, stirring for 5 hours at room temperature, filtering the reaction system, concentrating, adding water after concentrating, washing with ethyl acetate after stirring for dissolving, adding sodium chloride into the aqueous phase after washing, stirring for dissolving, extracting with dichloromethane, combining the organic phases, drying over anhydrous sodium sulfate, filtering under vacuum, concentrating, adding isopropanol and ethyl acetate, heating for dissolving, and cooling for crystallization.

In yet another aspect, the present invention provides use of the polyethylene glycol lipid in the delivery of a bioactive substance to a cell or an organ.

In still another aspect, the present invention provides use of the polyethylene glycol lipid in the preparation of a bioactive substance delivery system.

Furthermore, the bioactive substance may be a small molecular compound, a nucleic acid, an oligopeptide, etc. Preferably, the bioactive substance is a nucleic acid.

Furthermore, the bioactive substance is DNA or RNA.

Furthermore, the DNA includes a non-coding DNA (an antisense DNA) or a coding DNA.

Furthermore, the RNA includes an antisense RNA, an mRNA, a lncRNA, an miRNA, an siRNA, a piRNA, a gRNA, a tsRNA, etc.

Furthermore, the nucleic acid is used for preventing and/or treating cancer, inflammation, fibrotic disease, autoimmune disease, infection, psychiatric disorder, hematological disorder, chromosomal disease, genetic disease, connective tissue disease, digestive disease, ear-nose-throat disease, endocrine disease, eye disease, reproductive disease, heart disease, kidney disease, lung disease, metabolic disorder, oral disease, musculoskeletal disease, neonatal screening, nutritional disease, parasitic disease, skin disease, etc.

Furthermore, the present invention also provides use of the polyethylene glycol lipid in the delivery of an siRNA to a cell or an organ.

Furthermore, the present invention also provides use of the polyethylene glycol lipid in the preparation of a lipid or lipid nanoparticle delivery system.

Furthermore, the present invention also provides use of the polyethylene glycol lipid in the delivery of an mRNA vaccine to a cell or an organ.

Furthermore, the present invention also provides use of the polyethylene glycol lipid in the preparation of an mRNA vaccine. Preferably, the vaccine may be used for preventing cancer, virus infection, bacterial infection, fungal infection, etc. The virus infection includes, but is not limited to: norovirus, Ebola virus, coronavirus (including novel coronavirus SARS-CoV-2), cytomegalovirus, Dengue virus, Zika virus, coxsackievirus, enterovirus, hepatitis virus, herpes simplex virus, human papilloma virus, influenza virus, Marburg virus, measles virus, poliovirus, rabies virus, rotavirus, measles virus, etc.

In yet another aspect, the present invention provides a lipid mixture comprising a bioactive substance and the polyethylene glycol lipid of the present invention.

Furthermore, the method for preparing the lipid mixture comprises a heating method, a reverse evaporation method, or a mixing method.

Furthermore, the heating method comprises adding an organic solvent solution of the polyethylene glycol lipid into an aqueous solution of a bioactive substance to obtain a mixed solution, and heating the mixed solution at an appropriate temperature.

Preferably, the heating temperature is 25° C.-100° C. Preferably, the heating time is 10 minutes-24 hours.

Furthermore, the reverse evaporation method comprises mixing an aqueous solution of a bioactive substance with an organic solvent solution of a polyethylene glycol lipid compound to obtain a mixed solution.

Furthermore, the bioactive substance in the lipid mixture is mixed with polyethylene glycol lipid particles in a molar ratio of 1:1-100, and preferably, the bioactive substance in the lipid mixture is mixed with the polyethylene glycol lipid particles in a molar ratio of 1:5-30, e.g., 1:5, 1:10, 1:15, 1:20, 1:25, or 1:30.

In yet another aspect, the present invention provides a lipid nanoparticle comprising a bioactive substance and the polyethylene glycol lipid compound of the present invention.

Furthermore, the lipid nanoparticle further comprises one or more of a cationic lipid, a steroid lipid, and a neutral lipid.

Furthermore, the cationic lipid includes, but is not limited to: ((4-hydroxybutyl)azadialkyl)bis(hexane-6,1-diyl)bis(2-hexyldecanoate) (ALC-0315), octadecan-9-yl 8-((2-hydroxyethyl)(6-oxo-6-(undecyloxy)hexyl)amino)octanoate (SM-102), 1,2-dioleoyloxy-3-(trimethylammonium)propane (DOTAP), 313-[N—(N',N'-dimethylaminoethane)-carbamoyl]cholesterol (DC cholesterol), dimethyldioctadecylammonium (DDA), 1,2-dimyristoyl-3-trimethylammonium propane (DMTAP), dipalmitoyl(C16:0)trimethylammonium propane (DPTAP), distearoyltrimethylammonium propane (DSTAP), N-[1-(2,3-diallyloxy)propyl]-N,N,N-trimethylammonium chloride (DOTMA), N,N-dioleoyl-N,N-dimethylammonium chloride (DODAC), 1,2-dioleoyl-sn-trioxy-3-ethylphosphocholine (DOEPC), 1,2-dioleoyl-3-dimethylammonium propane (DODAP), 1,2-dioleyloxy-3-dimethylaminopropane (DLinDMA), etc.

Furthermore, the neutral lipid includes, but is not limited to: 1,2-distearoyl-sn-glycerol-3-phosphocholine (DSPC), 1,2-dipalmitoyl-sn-glycerol-3-phosphocholine (DPPC), 1,2-dioleoyl-sn-glycerol-3-phosphoethanolamine (DOPE), 1,2-dipalmitoyl-sn-glycerol-3-phosphoethanolamine (DPPE), 1,2-dimyristoyl-sn-glycero-3-phosphoethanolamine (DMPE), 2-dioleoyl-sn-glycero-3-phospho-(1'-rac-glycerol) (DOPG), oleoyl phosphatidylcholine (POPC), 1-palmitoyl-2-oleoyl phosphatidylethanolamine (POPE), etc.

Furthermore, the steroid lipid includes, but is not limited to, avenasterol, β-sitosterol, brassicasterol, ergocalciferol, campesterol, cholestanol, cholesterol, coprosterol, dehydrocholesterol, desmosterol, dihydroergocalciferol, dihydrocholesterol, dihydroergosterol, campesterol, epicholesterol, ergosterol, fucosterol, hexahydrosterol, hydroxycholesterol, lanosterol, photosterol, fucosterol, sitostanol, sitosterol, stigmastanol, stigmasterol, cholic acid, glycocholic acid, taurocholic acid, deoxycholic acid, and lithocholic acid, etc.

Furthermore, the lipid nanoparticle of the present invention comprises a bioactive substance, the polyethylene glycol lipid compound of the present invention, a cationic lipid, a steroid lipid, and a neutral lipid.

Furthermore, the molar ratio of the polyethylene glycol lipid compound, the cationic lipid, the steroid lipid and the neutral lipid in the lipid nanoparticle of the present invention is (0.5-5):(30-55):(30-55):(5-20). Preferably, the molar ratio of the polyethylene glycol lipid compound, the cationic lipid, the steroid lipid and the neutral lipid is (1-5):(35-50):(40-50):(8-15). More preferably, the molar ratio of the polyethylene glycol lipid compound, the cationic lipid, the steroid lipid and the neutral lipid is 1.5:50:38.5:10.

Furthermore, in the lipid nanoparticle of the present invention, the cationic lipid is AC-0315, and/or the steroid lipid is cholesterol, and/or the neutral lipid is DSPC.

Furthermore, in the lipid nanoparticle of the present invention, the cationic lipid is SM-102, and/or the steroid lipid is cholesterol, and/or the neutral lipid is DSPC.

The lipid nanoparticle of the present invention may be prepared by using a conventional method for preparing a lipid nanoparticle in the art, e.g., high pressure homogenization, emulsion precipitation, ultrasonic dispersion, etc.

The present invention also provides a pharmaceutical composition, wherein the pharmaceutical composition comprises the lipid mixture of the present invention or the lipid nanoparticle of the present invention, and a pharmaceutically acceptable excipient.

The pharmaceutically acceptable excipient of the present invention is, for example, a carrier, an adjuvant, a diluent, etc.

The lipid mixture, the lipid nanoparticle or the pharmaceutical composition of the present invention may deliver the bioactive substance by oral administration, inhalation or injection.

The present invention also provides a method for delivering a bioactive substance, which comprises administering to a human in need thereof the lipid mixture, the lipid nanoparticle or the pharmaceutical composition of the present invention.

DETAILED DESCRIPTION

Figure 1:
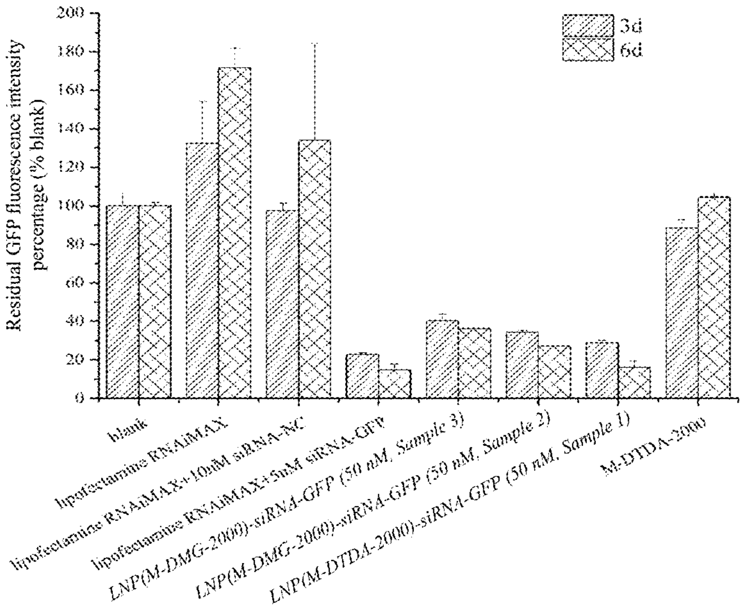
FIG. 1 shows a bar graph showing residual GFP fluorescence intensity percentage of each group of samples at day 3 and day 6 after transfection.

Technical solutions in the embodiments of the present invention will be described clearly and completely below with reference to the drawings. It is apparent that the described embodiments are only a part of the embodiments of the present invention, but not all of them. Based on the examples of the present invention, all other examples obtained by those of ordinary skill in the art without creative work shall fall within the protection scope of the present invention.

The term "nucleic acid" described herein refers to a polymer containing at least two deoxyribonucleotides or ribonucleotides in either single- or double-stranded form and includes DNA, RNA, and hybrids thereof.

The term "lipid" described herein refers to a group of organic compounds that include, but are not limited to, esters of fatty acids and are generally characterized by being poorly soluble in water, but soluble in many organic solvents.

The term "cationic lipid" described herein refers to a lipid molecule capable of being positively charged.

The term "neutral lipid" described herein refers to an uncharged, non-phosphoglyceride lipid molecule.

The term "polyethylene glycol lipid" described herein refers to a molecule comprising a lipid portion and a polyethylene glycol portion.

The term "lipid nanoparticle" described herein refers to a particle having at least one nanoscale dimension, which comprises at least one lipid.

The term "vaccine" described herein refers to a composition suitable for application to an animal (including a human), which induces an immune response after administration with a strength sufficient to help prevent, improve, or cure clinical diseases caused by microbial infections as a minimum.

The term "delivery system" described herein refers to a formulation or composition that regulates the spatial, temporal and dose distribution of a biologically active ingredient in an organism.

Example 1: Preparation of Polyethylene Glycol Lipid (M-DTDA-2000)

1) M-CM-2000 (Methoxy PEG Acetic Acid, mPEG-COOH, 2 g, 1 mmol) and ditetradecylamine (0.576 g, 1.4 mmol) were added to a 100-mL single-necked flask containing dichloromethane (20 mL), and dissolved with stirring, then DIEA (260 mg, 2 mmol) and HATU (760 mg, 2 mmol) were sequentially added, and the reaction system was stirred at room temperature for 5 h. The reaction system was filtered, the mother liquor was concentrated under vacuum, 40 mL of purified water was added after the concentration, and the mother liquor was washed for 3 times with ethyl acetate after being dissolved with stirring, wherein 40 mL of purified water was used for each time. After washing, 6 g of sodium chloride was added to the aqueous phase and the mixture was dissolved with stirring, and the aqueous phase was extracted with dichloromethane (20 mL×2). The organic phases were combined, dried over anhydrous sodium sulfate, and filtered under vacuum. The filtrate was concentrated under vacuum, 30 mL of isopropanol and 10 mL of ethyl acetate were added, and the reaction system was heated to 40° C. for dissolving, then cooled to −15° C. for crystallization, and filtered under vacuum. The filter cake was dried under vacuum to give 1.4 g of a white solid (M-DTDAM-2000) in a yield of 58.3%.

$^1$H-NMR (400 MHz, DMSO) δ: 4.1 (2H, s), 3.55 (180H, m), 3.26 (3H, s), 3.18 (4H, t), 1.46 (4H, m), 1.24 (44H, m), 0.86 (6H, t).

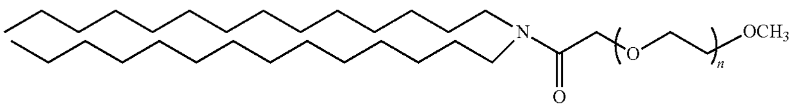

M-DTDAM-2000 (MW 2000)

2) $LiAlH_4$ (380 mg, 10 mmol) was slowly added to a three-necked flask containing 30 mL of tetrahydrofuran in an ice-water bath under nitrogen atmosphere. M-DTDAM-2000 (2 g, 1 mmol) was dissolved in 10 mL of tetrahydrofuran, and the reaction solution was slowly and dropwise added to a reaction flask. 10 mL of purified water was dropwise added to the reaction system after 3 hours, the system was filtered through celite, and the filtrate was concentrated under vacuum. 20 mL of isopropanol was added, and the system was heated to 40° C. for dissolving, then cooled in an ice-water bath for crystallization, and filtered under vacuum. The filter cake was dried under vacuum to give 1.1 g of a white solid (M-DTDA-2000) in a yield of 55%.

$^1$H-NMR (400 MHz, DMSO) δ: 3.55 (180H, m), 3.24 (3H, s), 2.36 (4H, t), 1.34 (4H, m), 1.24 (44H, m), 0.86 (6H, t).

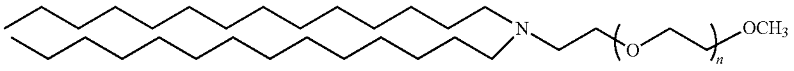

M-DTDA-2000 (MW 2000)

Example 2: Preparation of Polyethylene Glycol Lipid (M-DTDA-2000(p))

1) M-PA-2000 (Methoxy PEG Propionic Acid, mPEG-$CH_2CH_2COOH$, 2 g, 1 mmol) and ditetradecylamine (0.617 g, 1.5 mmol) were added to a 100-mL single-necked flask containing dichloromethane (20 mL), and dissolved with stirring, then DIEA (260 mg, 2 mmol) and HATU (760 mg, 2 mmol) were sequentially added, and the reaction system was stirred at room temperature for 5 h. The reaction system was filtered, the mother liquor was concentrated under vacuum, 40 mL of purified water was added after the concentration, and the mother liquor was washed for 3 times with ethyl acetate after being dissolved with stirring, wherein 40 mL of purified water was used for each time. After washing, 6 g of sodium chloride was added to the aqueous phase and the mixture was dissolved with stirring, and the aqueous phase was extracted with dichloromethane (20 mL×2). The organic phases were combined, dried over anhydrous sodium sulfate, and filtered under vacuum. The filtrate was concentrated under vacuum, 30 mL of isopropanol and 10 mL of ethyl acetate were added, and the reaction system was heated to 40° C. for dissolving, then cooled to −15° C. for crystallization, and filtered under vacuum. The filter cake was dried under vacuum to give 1.32 g of a white solid (M-DTDAM-2000(p)) in a yield of 55%.

$^1$H-NMR (400 MHz, DMSO) δ: 3.55 (180H, m), 3.26 (3H, s), 3.18 (4H, t), 2.45 (2H, t), 1.46 (4H, m), 1.24 (44H, m), 0.86 (6H, t).

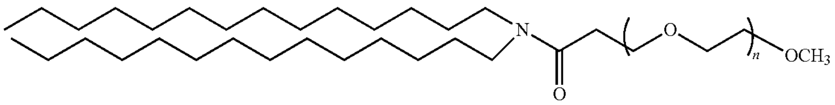

M-DTDAM-2000(p) (MW 2000)

2) $LiAlH_4$ (380 mg, 10 mmol) was slowly added to a three-necked flask containing 30 mL of tetrahydrofuran in an ice-water bath under nitrogen atmosphere. M-DTDAM-2000(p) (2 g, 1 mmol) was dissolved in 10 mL of tetrahydrofuran, and the reaction solution was slowly and dropwise added to a reaction flask. 10 mL of purified water was dropwise added to the reaction system after 3 hours, the system was filtered through celite, and the filtrate was concentrated under vacuum. 20 mL of isopropanol was added, and the system was heated to 40° C. for dissolving, then cooled in an ice-water bath for crystallization, and filtered under vacuum. The filter cake was dried under vacuum to give 1.15 g of a white solid (M-DTDA-2000(p)) in a yield of 57.5%.

$^1$H-NMR (400 MHz, DMSO) δ: 3.55 (180H, m), 3.24 (3H, s), 2.36 (4H, t), 1.34 (4H, m), 1.24 (44H, m), 0.86 (6H, t).

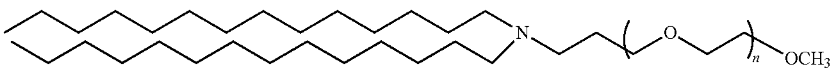

M-DTDA-2000(p) (MW 2000)

Example 3: Fluorescence Inhibitory Effect of PEG-Lipid/Cationic Lipid/Neutral Lipid/Steroid Lipid-siRNA Nanoparticles Delivering siRNA in MDA-MB-231-GFP Cells The formula and preparation method for PEG-lipid/cationic lipid/neutral lipid/steroid lipid-siRNA nanoparticles in each group were as follows:

ALC-0315/M-DTDA-2000 (prepared in Example 1)/DSPC/cholesterol was dissolved in absolute ethanol at a molar ratio of 50%/1.5%/10%/38.5% to prepare a 10 mmol/L mixed solution, and then a citric acid buffer solution with PH=4 was added to prepare a 30% ethanol-citric acid solution containing four types of lipids, which was filtered through a 0.1 μm filter membrane for later use. siRNA-GFP (target sequence as shown in SEQ ID NO: 1: 5'-GGCUACGUCCAGGAGCGCACC-3') was dissolved at a concentration of 2 mg/mL in a 30% lipid-free ethanol-citric acid solution, and then mixed with the 30% ethanol-citric acid solution containing four types of lipids as described above according to a mass ratio of siRNA-GFP:lipid of 0.06:1. The resulting mixture was incubated for 30 min and dialyzed with PBS at PH=7.4 for more than 16 h to obtain LNP(M-DTDA-2000)-siRNA-GFP (sample 1).

ALC-0315/M-DMG-2000 (commercially available from Methoxy PEG Dimyristoyl-rac-glycero, JenKem Technology Co., Ltd.)/DSPC/cholesterol was dissolved in absolute ethanol at a molar ratio of 50%/1.5%/10%/38.5% to prepare a 10 mmol/L mixed solution, and then a citric acid buffer solution with PH=4 was added to prepare a 30% ethanol-citric acid solution containing four types of lipids, which was filtered through a 0.22 μm filter membrane for later use. siRNA-GFP (target sequence as shown in SEQ ID NO: 1: 5'-GGCUACGUCCAGGAGCGCACC-3') was dissolved at a concentration of 2 mg/mL in a 30% lipid-free ethanol-citric acid solution, and then mixed with the 30% ethanol-citric acid solution containing four types of lipids as described above according to a mass ratio of siRNA-GFP: lipid of 0.06:1.

The above solution was incubated for 30 min and dialyzed with PBS at PH=7.4 for more than 16 h to prepare LNP(M-DMG-2000)-siRNA-GFP (sample 2).

The above solution was used to prepare LNP(M-DMG-2000)-siRNA-GFP (sample 3) using a microfluidic device (model MPE-L2, Suzhou Aitesen Pharmaceutical Equipment Co., Ltd.).

The structure of M-DMG-2000 was as follows:

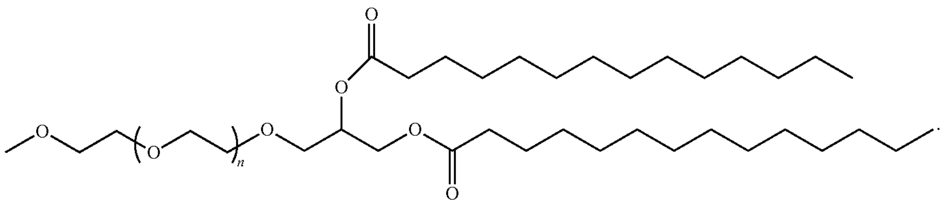

MW 2000

Cell culture: MDA-MB-231-GFP cell culture was carried out using RPMI-1640 medium containing 10% fetal bovine serum, 100 U/mL penicillin, and 0.1 mg/mL streptomycin in an incubator with 5% $CO_2$ at 37° C., and passaging was carried out every 3 days. 24 h before transfection, MDA-MB-231-GFP cells were digested and plated in a 24-well plate at a density of $1.5\times10^5$ cell/well, and the cells were further cultured for 24 h.

Reagent preparation in lipofectamine RNAiMAX groups: firstly, lipofectamine RNAiMAX was mixed with ½ volumes of opti-MEM according to the recommended amount of the instruction, 20 μM siGFP/siNC was mixed with ½ volumes of opti-MEM according to the calculated volume, and after standing for 5 min, the two were mixed to prepare a 10× working solution which was left to stand at room temperature. In the single lipofectamine RNAiMAX group, the same amount of lipofectamine RNAiMAX and opti-MEM were directly mixed and stood for later use.

LNP preparation in each group: the prepared LNP was diluted to 10× working concentration with opti-MEM and left to stand at room temperature for 30 min. Transfection: the culture media in the cell wells were discarded, and then 400 μL of RPMI-1640+10% FBS culture medium was added. Then 100 μL each of the above transfection reagents was added. Samples were taken respectively at 3 d and 6 d after transfection, the culture medium of each well was removed, the samples were washed once with PBS, then 300 μL of cell lysate was added and reacted for 10 min at 37° C., then samples from each well were taken out, and centrifuged at 10000×g at 4° C. for 10 min, and the supernatant was taken for the detection of protein concentration and fluorescence intensity.

Protein Standard Curve Preparation and Protein Concentration Detection:

Preparation of working solution: according to the number of standards and samples, 50 volumes of BCA reagent and 1 volume of Cu reagent (50:1) were prepared into a BCA working solution which was mixed well (there could be turbidity during mixing, but it would disappear after mixing). The BCA working solution was stable within 24 h at room temperature.

Dilution of a standard: 10 μL of BSA standard was diluted to 100 μL with PBS (samples could be diluted with PBS in general) to obtain a final concentration of 0.5 mg/mL. The standard was added to the protein standard wells of a 96-well plate at 0, 2, 4, 6, 8, 12, 16, 20 μL, and PBS was added to make up to 20 μL.

20 μL of sample was added to the sample wells of a 96-well plate. At the same time, a blank control was set, and 20 μL of cell lysate was added into the well plate. 200 μL of BCA working solution was added to each well, and the mixture was left at 37° C. for 15-30 minutes. A562 nm was measured by a microplate reader, and the protein concentration was calculated from the standard curve.

Fluorescence intensity detection: 100 μL of each sample was added into a black light-tight 96-well plate, a blank control was set, and 20 μL of cell lysate was added into the well plate. The detection was carried out by using a microplate reader, and the excitation light wavelength was set as 488 nm and the emission light wavelength was set as 509 nm.

Data calculation: when each sample was calculated, the blank hole reading value was first subtracted to reduce background interference. After the fluorescence value of each sample was normalized with the protein concentration, the mean value of the blank group was normalized to obtain the residual GFP fluorescence intensity percentage data. The results are shown in Table 1 and FIG. 1.

TABLE 1

| | 3 d mean fluorescence intensity percentage | | 6 d mean fluorescence intensity percentage | |
|---|---|---|---|---|
| group | mean | SD | mean | SD |
| blank | 100.00 | 6.65 | 100.00 | 1.91 |
| lipofectamine RNAiMAX | 132.54 | 21.81 | 171.68 | 10.16 |
| lipofectamine RNAiMAX + 10 nM siRNA-NC | 97.51 | 4.01 | 134.07 | 50.48 |
| lipofectamine RNAiMAX + 5 nM siRNA-GFP | 22.81 | 0.95 | 14.77 | 3.08 |
| LNP(M-DMG-2000)-siRNA-GFP (50 nM sample 3) | 40.21 | 3.65 | 36.30 | 2.98 |
| LNP(M-DMG-2000)-siRNA-GFP (50 nM sample 2) | 34.50 | 0.74 | 27.24 | 1.02 |
| LNP(M-DTDA-2000)-siRNA-GFP (50 nM sample 1) | 28.91 | 1.13 | 16.14 | 3.41 |
| M-DTDA-2000 | 88.56 | 4.14 | 104.61 | 2.04 |

At day 3 and day 6 after transfection, the GFP fluorescence intensity of each LNP group and lipofectamine RNAiMAX+5 nM siGFP group decreased significantly, showing a good inhibitory effect. The LNP(M-DTDA-2000)-siRNA-GFP group (sample 1) achieved a similar effect to the lipofectamine RNAiMAX+5 nM siRNA-GFP group, and had a better inhibitory effect than the LNP(M-DMG-2000)-siRNA-GFP group (samples 2 and 3).

The results show that after siRNA-GFP was delivered into cells by lipid nanoparticles of each group prepared from M-DTDA-2000/ALC-0315/DSPC/cholesterol and siRNA-GFP, the lipid nanoparticles had a significant and continuous inhibitory effect on GFP mRNA, and also, the total gene inhibitory effect of the lipid nanoparticle group prepared from M-DTDA-2000 was better than that of other groups.

Example 4: Fluorescence Enhancement Effect of PEG-Lipid/Cationic Lipid/Neutral Lipid/Steroid Lipid-mRNA Nanoparticles for Delivering mRNA in 293T Cells LNP combination ingredients: cationic lipid (ALC0315)/PEG-lipid component (M-DMG-2000, M-DTDA-2000 or M-DTDAM-2000)/DSPC/cholesterol at a molar ratio of 50%/1.5%/10%/38.5%. The solution of each component with the concentration of 10 mM was prepared and dissolved in absolute ethanol. 258 μL of cationic lipid solution, 7.68 μL of PEG component solution, 51.6 μL of DSPC solution and 198.6 μL of cholesterol solution were mixed. After vortex oscillation and uniform mixing, the mixture was filtered with a 0.22 μM filter membrane to prepare an LNP solution for later use.

ALC0315 and M-DMG-2000 were both commercially available from JenKem Technology Co., Ltd.

M-DTDA-2000 and M-DTDAM-2000 were prepared according to Example 1.

Three kinds of LNP solutions were prepared, with the following composition (wherein DMG represented M-DMG-2000, DTDA represented M-DTDA-2000, and DTDAM represented M-DTDAM-2000, all of which were PEG-lipid): DSPC+cholesterol+ALC0315+DMG/DTDA/DTDAM;

the ratio of LNP solution to GFP mRNA diluent was 1:3.

Total GFP mRNA diluent volume 150 μL: 10 μg of GFP mRNA (i.e., 10 μL of GFP mRNA) diluted in 140 μL of PBS citrate at pH of 4.0. 150 μL of GFP mRNA diluent and 51.5 μL of LNP solution were vortexed, uniformly mixed, and left to stand at room temperature for 30 min. 0.5 μg of GFP mRNA (i.e., 10 μL GFP mRNA-LNP mixed solution) was diluted with 40 μL serum-free diluent (basal medium DMEM), and the resulting diluent was vortexed and uniformly mixed for 10 s to prepare 50 μL of GFP mRNA transfection mixture.

Positive Control:

50 μL of mRNA buffer was added into 0.5 μg of GFP mRNA according to the proportion of the instruction, the resulting mixture was vortexed and uniformly mixed for 10 s to prepare a GFP mRNA diluent; 1 μL of jetMESSENGER reagent (mRNA/jetMESSENGER ratio was 1:2) was added and vortexed for 10 s, rotated and then incubated at room temperature for 15 min.

Naked mRNA Control:

0.5 μg of GFP mRNA was added to 50 μL of DEME medium, and vortexed and uniformly mixed for 10 s to prepare a GFP mRNA diluent.

Blank Control: 50 μL of DEME Medium.

Plating: 293T cells were seeded onto a 24-well plate one day in advance, at preferably around 12000-50000 cell/well at the time of transfection, and the total amount of whole medium (no antibiotics and containing 10% serum) before transfection was 0.5 mL/well. Culture was carried out in a 24-well plate with 5% $CO_2$ at 37° C. for one day, wherein 3 replicate wells were set.

Transfection: 50 μL of GFP mRNA transfection mixture was dropped onto cells with 0.5 mL of whole medium (no antibiotics and containing 10% serum), and the culture plate was gently moved back and forth, mixed well, and cultured in an incubator with 5% $CO_2$ at 37° C.

Figure 2:
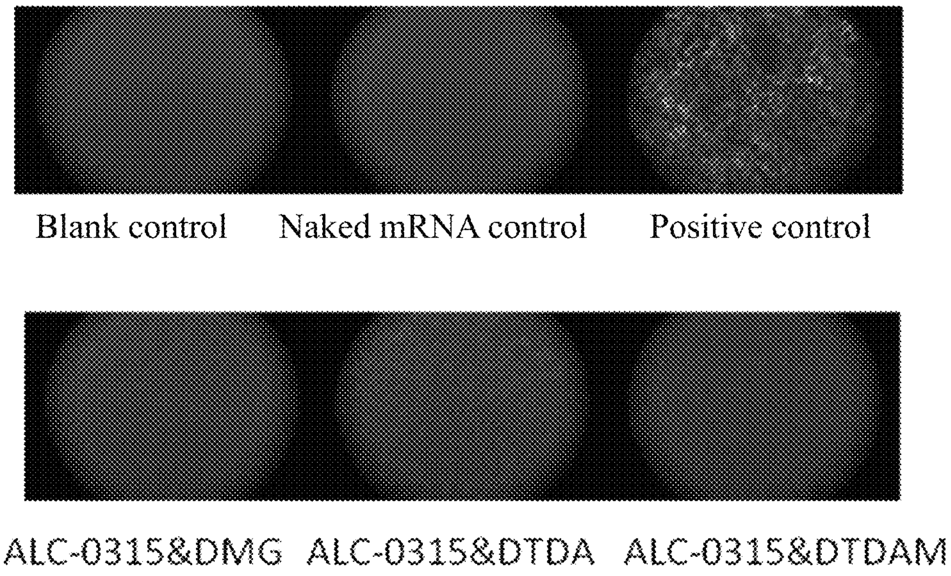
FIG. 2 shows the expression of GFP protein observed under a fluorescence microscope.

Fluorescent protein expression was observed under a fluorescent microscope: the state of the cells was observed 4 h after transfection, and the cells were further cultured for 24-72 h, and the expression of GFP protein was observed under a fluorescent microscope and recorded by photography (FIG. 2).

Figure 3:
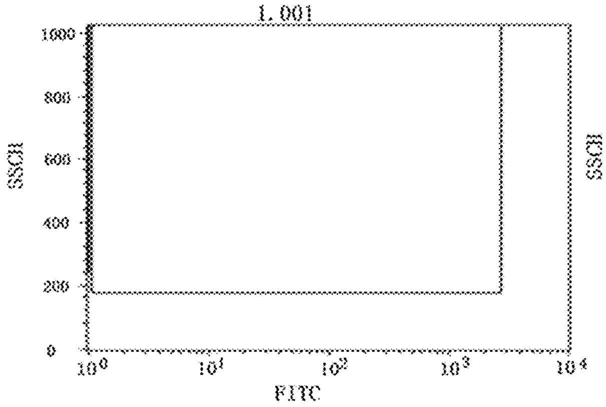
FIG. 3 shows a graph showing characterization of the proportion of GFP-expressing positive cells after transfection by flow cytometry.
Figure 3:
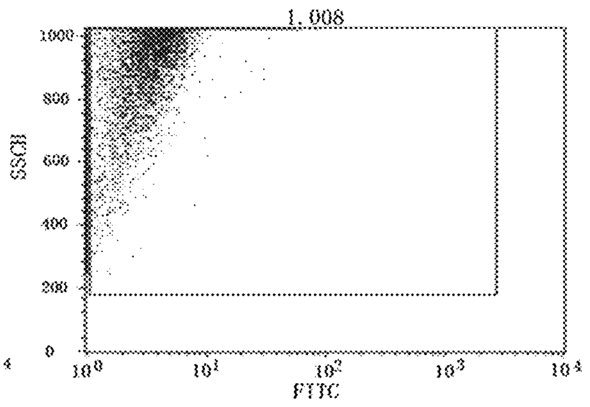
Figure 3:
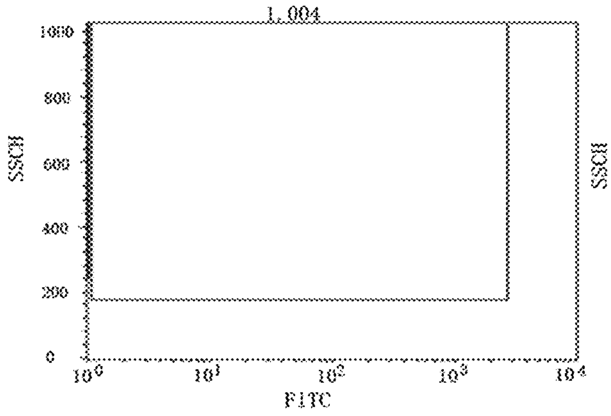
Figure 3:
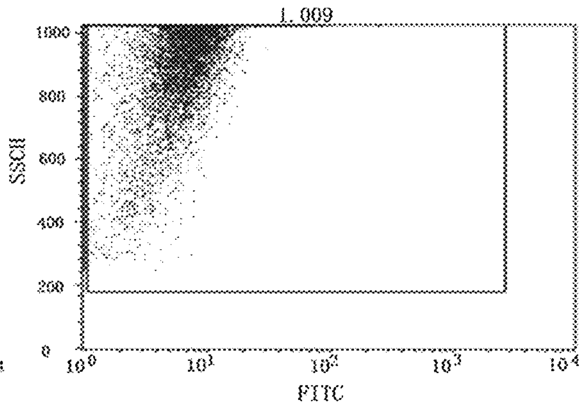
Figure 3:
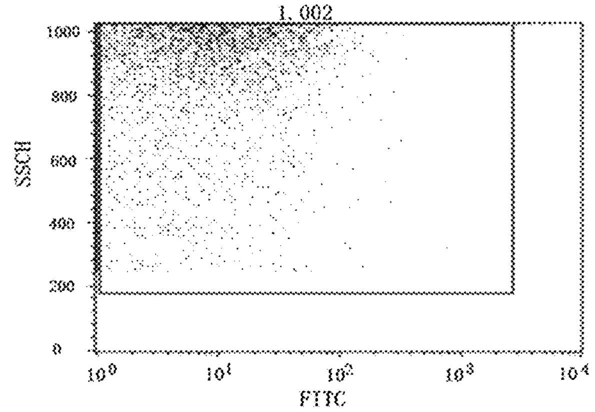
Figure 3:
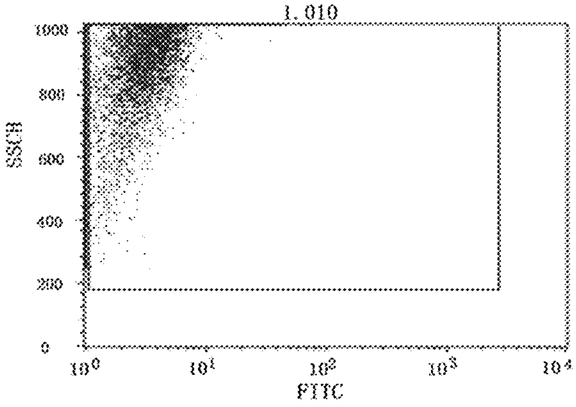

Characterization of the proportion of GFP-expressing positive cells after transfection by flow cytometry is shown in FIG. 3

The results of fluorescence microscopy and flow cytometry are shown in Table 2:

TABLE 2

| Test number | Sample code | Mean fluorescence intensity | Proportion of positive cells (%) |
|---|---|---|---|
| 1 | Blank control | 1 | 0 |
| 2 | Positive control | 51.44 | 90.23 |
| 3 | Naked mRNA control | 1 | 0 |
| 4 | ALC-0315&DMG | 5.55 | 80.33 |
| 5 | ALC-0315&DTDA | 11.51 | 86.99 |
| 6 | ALC-0315&DTDAM | 5.11 | 81.99 |

The preferred embodiments of the present invention are described in detail above, which, however, are not intended to limit the present invention. Within the scope of the technical concept of the present invention, various simple modifications can be made to the technical solution of the present invention, all of which will fall within the protection scope of the present invention.

In addition, it should be noted that the various specific technical features described in the above specific embodiments can be combined in any suitable manner where the features do not contradict each other. In order to avoid unnecessary repetition, such combinations will not be illustrated separately.

The invention claimed is:

1. A polyethylene glycol lipid having a structure of formula I below:

Formula I

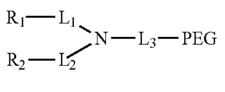

wherein $R_1$ and $R_2$ are identical or different long chain hydrocarbyl, and the long chain hydrocarbyl contains 11 to 17 carbon atoms;

PEG is a polyethylene glycol chain; and $L_1$, $L_2$ and $L_3$ are absent or are in-vivo non-cleavable linkers.

2. The polyethylene glycol lipid according to claim 1, wherein the long chain hydrocarbyl contains 14 carbon atoms.

3. The polyethylene glycol lipid according to claim 1, wherein the polyethylene glycol chain comprises a repeating unit of $-(OCH_2CH_2)_n-$, wherein the n is selected from integers of 20 to 300.

4. The polyethylene glycol lipid according to claim 3, wherein the polyethylene glycol chain is $-(OCH_2CH_2)_n-X$, wherein X is a terminal group of the polyethylene glycol chain, and is selected from methyl, methoxy, hydroxyl, amino, thiol, and maleimide.

5. The polyethylene glycol lipid according to claim 1, wherein the in-vivo non-cleavable linker is C1 to C10 alkylene.

6. The polyethylene glycol lipid according to claim 1, wherein the polyethylene glycol lipid has a structure of formula II below:

Formula II

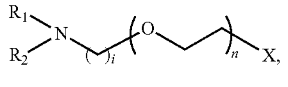

wherein $R_1$ and $R_2$ are as defined in claim 1;

X is a terminal group of the polyethylene glycol chain, and is selected from methyl, methoxy, hydroxyl, amino, thiol, and maleimide;

n is selected from integers of 20 to 300;

i is selected from integers of 2 to 7.

7. The polyethylene glycol lipid according to claim 1, wherein the polyethylene glycol lipid has a structure below:

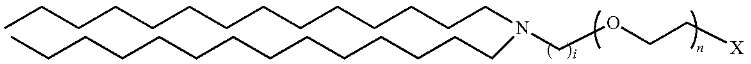

wherein, X is a terminal group of the polyethylene glycol chain, and is selected from methyl, methoxy, hydroxyl, amino, thiol, and maleimide;

n is selected from integers of 20 to 300;

i is selected from integers of 2 to 7.

8. A delivery system, wherein the delivery system comprises a bioactive substance and the polyethylene glycol lipid according to claim 1.

9. The delivery system according to claim 8, wherein the bioactive substance is a nucleic acid.

10. The delivery system according to claim 8, wherein the bioactive substance delivery system is a lipid or lipid nanoparticle delivery system.

11. The delivery system according to claim 8, wherein the bioactive substance delivery system is an mRNA vaccine.

12. A lipid nanoparticle, wherein the lipid nanoparticle comprises a bioactive substance and the polyethylene glycol lipid compound according to claim 1.

13. The lipid nanoparticle according to claim 12, wherein the lipid nanoparticle further comprises a cationic lipid, a steroid lipid, and a neutral lipid.

14. The lipid nanoparticle according to claim 13, wherein the cationic lipid is selected from ((4-hydroxybutyl)azadialkyl)bis(hexane-6,1-diyl)bis(2-hexyldecanoate) (ALC-0315), octadecan-9-yl 8-((2-hydroxyethyl) (6-oxo-6-(undecyloxy)hexyl) amino)octanoate (SM-102), 1,2-dioleoyloxy-3-(trimethylammonium)propane (DOTAP), 313-[N—(N',N'-dimethylaminoethane)-carbamoyl]cholesterol (DC cholesterol), dimethyldioctadecylammonium (DDA), 1,2-dimyristoyl-3-trimethylammonium propane (DMTAP), dipalmitoyl(C16: 0)trimethylammonium propane (DPTAP), distearoyltrimethylammonium propane (DSTAP), N-[1-(2,3-diallyloxy) propyl]-N,N,N-trimethylammonium chloride (DOTMA), N,N-dioleoyl-N,N-dimethylammonium chloride (DODAC), 1,2-dioleoyl-sn-trioxy-3-ethylphosphocholine (DOEPC), 1,2-dioleoyl-3-dimethylammonium propane (DODAP), 1,2-dioleyloxy-3-dimethylaminopropane (DLinDMA);

the neutral lipid is selected from 1,2-distearoyl-sn-glycerol-3-phosphocholine (DSPC), 1,2-dipalmitoyl-sn-glycerol-3-phosphocholine (DPPC), 1,2-dioleoyl-sn-glycerol-3-phosphoethanolamine (DOPE), 1,2-dipalmitoyl-sn-glycerol-3-phosphoethanolamine (DPPE), 1,2-dimyristoyl-sn-glycero-3-phosphoethanolamine (DMPE), 2-dioleoyl-sn-glycero-3-phospho-(1'-rac-glycerol) (DOPG), oleoyl phosphatidylcholine (POPC), 1-palmitoyl-2-oleoyl phosphatidylethanolamine (POPE);

the steroid lipid is selected from avenasterol, B-sitosterol, brassicasterol, ergocalciferol, campesterol, cholestanol, cholesterol, coprosterol, dehydrocholesterol, desmosterol, dihydroergocalciferol, dihydrocholesterol, dihydroergosterol, campesterol, epicholesterol, ergosterol, fucosterol, hexahydrosterol, hydroxycholesterol, lanosterol, photosterol, fucosterol, sitostanol, sitosterol, stigmastanol, stigmasterol, cholic acid, glycocholic acid, taurocholic acid, deoxycholic acid, and lithocholic acid.

* * * * *